US00PP21289P3

(12) United States Plant Patent
Probasco et al.

(10) Patent No.: US PP21,289 P3
(45) Date of Patent: Sep. 14, 2010

(54) HOP PLANT NAMED 'HBC 394'

(50) Latin Name: *Humulus lupulus*
Varietal Denomination: HBC 349

(75) Inventors: Eugene G. Probasco, Yakima, WA (US); Jason Perrault, Toppenish, WA (US)

(73) Assignee: Hop Breeding Company, L.L.C., Yakima, WA (US)

( * ) Notice: Subject to any disclaimer, the term of this patent is extended or adjusted under 35 U.S.C. 154(b) by 0 days.

(21) Appl. No.: 12/321,653

(22) Filed: Jan. 23, 2009

(65) Prior Publication Data

US 2009/0193555 P1 Jul. 30, 2009

Related U.S. Application Data

(60) Provisional application No. 61/062,531, filed on Jan. 24, 2008.

(51) Int. Cl.
*A01H 5/00* (2006.01)

(52) U.S. Cl. ..... Plt./236

(58) Field of Classification Search ..... Plt./236
See application file for complete search history.

*Primary Examiner*—Susan B McCormick Ewoldt
(74) *Attorney, Agent, or Firm*—Ballew Law

(57) ABSTRACT

A new hop plant named 'HBC 394' is disclosed. The cones of 'HBC 394' mature in early September, and yield a crop of 1200 to 1600 pounds per acre. 'HBC 394' is used in brewing for its bittering and aromatic properties.

6 Drawing Sheets

Genus and species: *Humulus lupulus.*
Variety denomination: HBC 394.

STATEMENT REGARDING FEDERALLY SPONSORED RESEARCH OR DEVELOPMENT

None.

BACKGROUND OF THE INVENTION

'HBC 394' is a product of a controlled breeding program carried out by the inventor in the Yakima Valley of Washington state. 'HBC 394' was one of several seedlings resulting from a cross made in 1990 of female parent '8801-02' ('Hallertauer mittlefrueh'×'853-144M') (not patented) and male parent '8801-01M ('Hallertauer mittlefrueh'×'853-144M') (not patented). A single plant of 'HBC 394' was selected in 1992, and in 1993 was expanded to four plants which were then planted in the area of Toppenish, Wash. The plants were observed and evaluated for several years, and in 2003 were expanded to 21 plants for further observation and evaluation in the Toppenish, Wash. area. A two acre test plot of 'HBC 394' was established in 2007. Throughout several generations of asexual propagation by softwood cuttings at a greenhouse facility in Yakima, Wash., 'HBC 394' has been observed to retain its distinctive characteristics and remain true to type. 'HBC 394' is distinguished from other known cultivars with hop cones containing a high alpha acid, low cohumulone acid combination. In addition, 'HBC 394' has a distinct citrus aromatic property.

'HBC 394 is distinguishable from its parent plants ('8801-02' and '8801-01M.') 'HBC 394' is distinguished from its male parent '8801-01M', with flowers that develop into mature hop cones without producing pollen, while the flowers of '8801-01M' produce pollen without developing into mature hop cones.

Table 1. sets forth some of the distinguishing characteristics of 'HBC 394' as compared to '8801- 02.'

TABLE 1

Comparison of 'HBC 394 to '8801-02'

| | 'HBC 394 | '8801-02' |
|---|---|---|
| Alpha Acids % | 11-13 | 9-11 |
| Beta Acids % | 3.4-4.5 | 2.5-3.5 |
| Cohumulone % | 22-24 | NA |
| Maturity | Mid Season | Early Season |

BRIEF DESCRIPTION OF THE PHOTOGRAPHS

Figure 1:
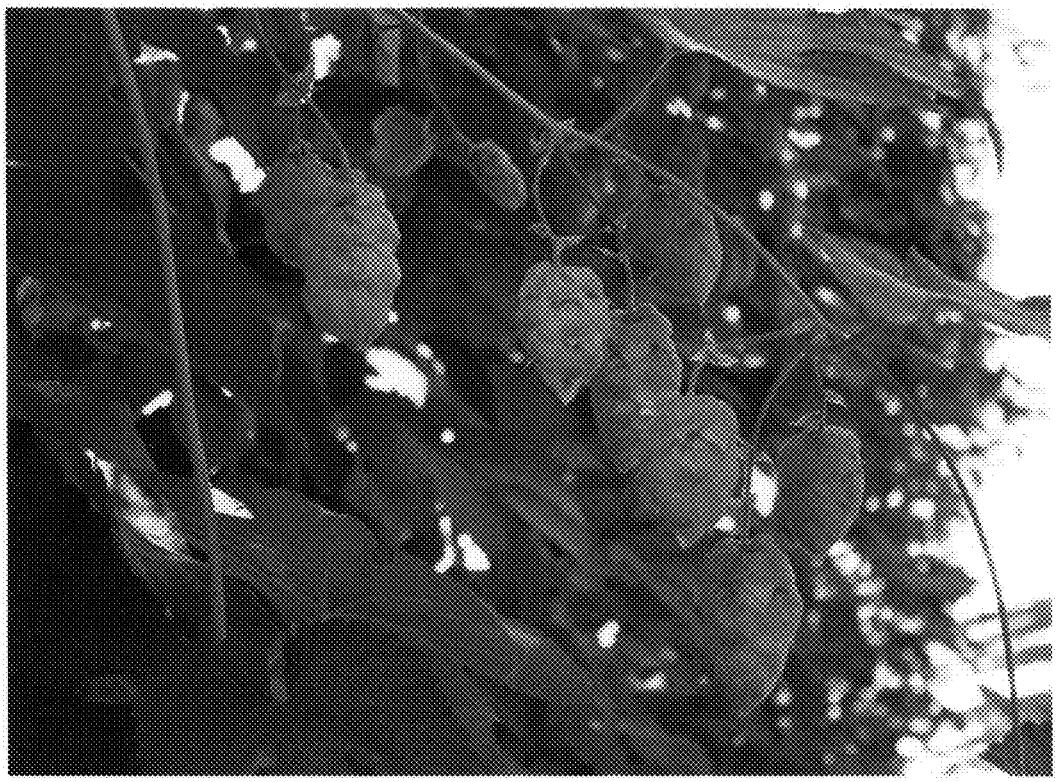
Figure 2:
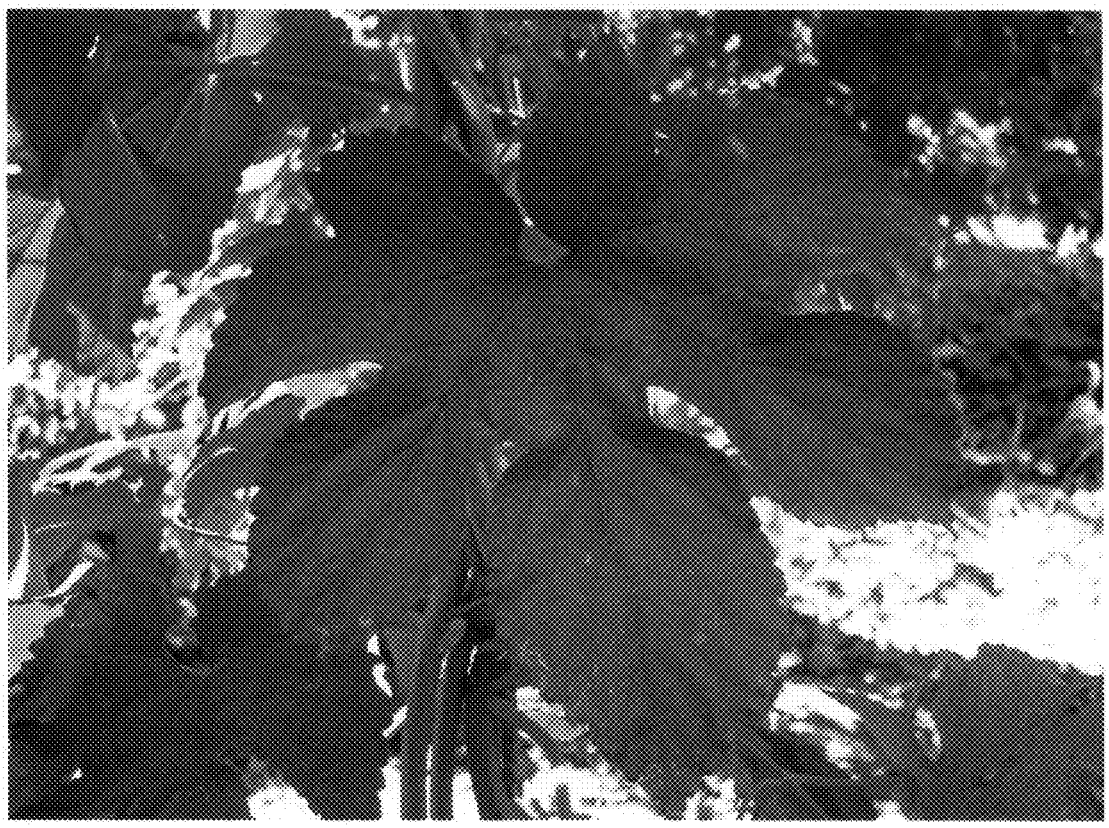
Figure 3:
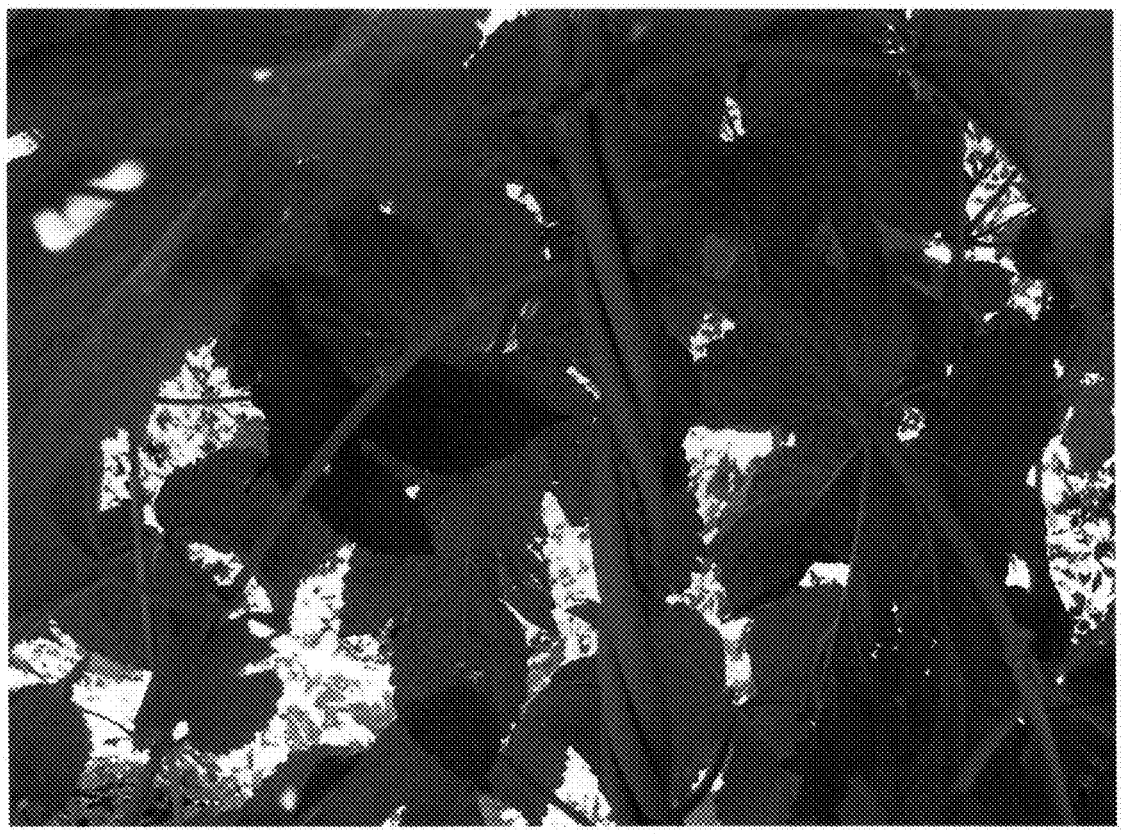
Figure 4:
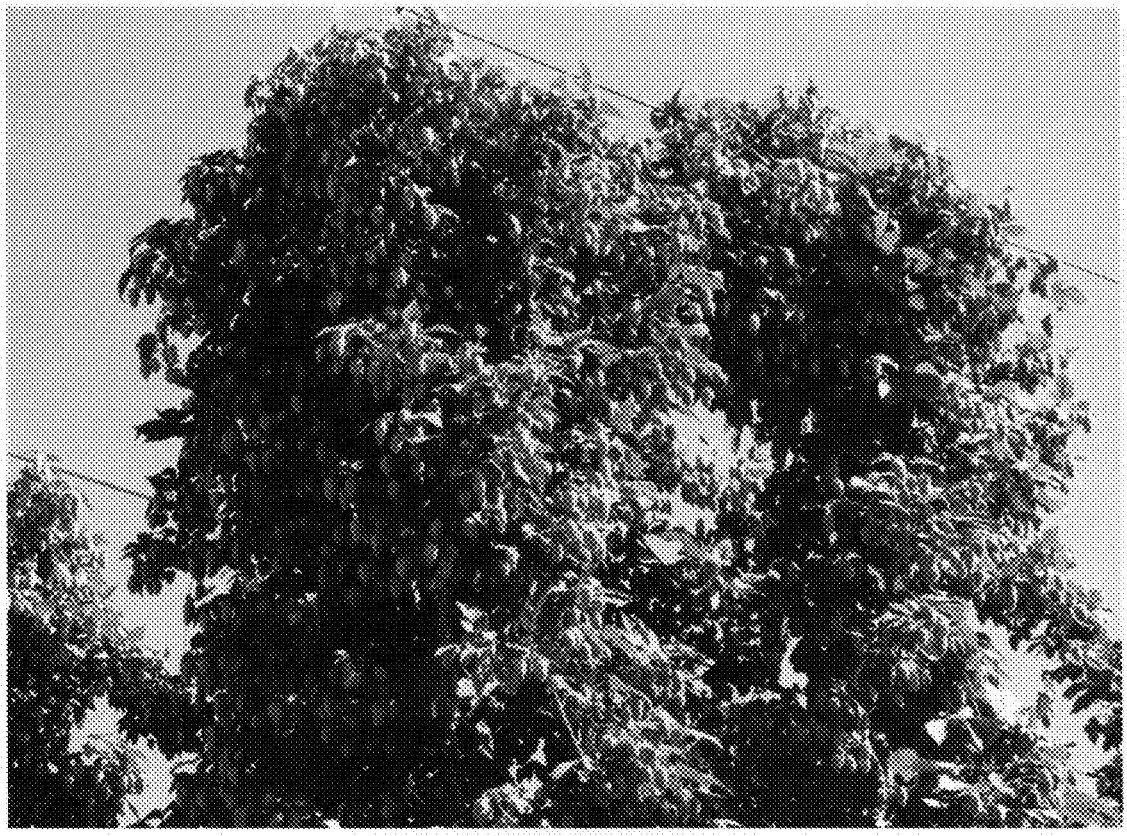
Figure 5:
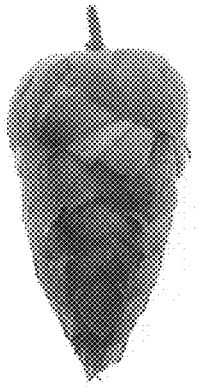
Figure 6:
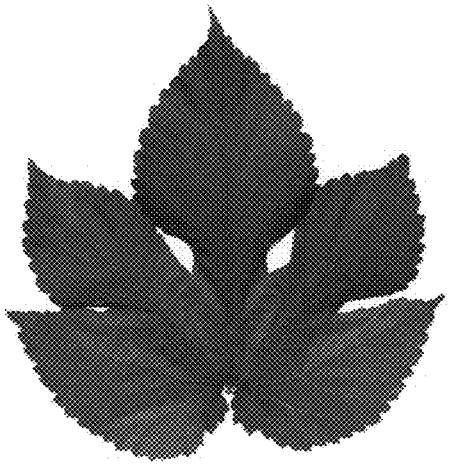
Figure 7:
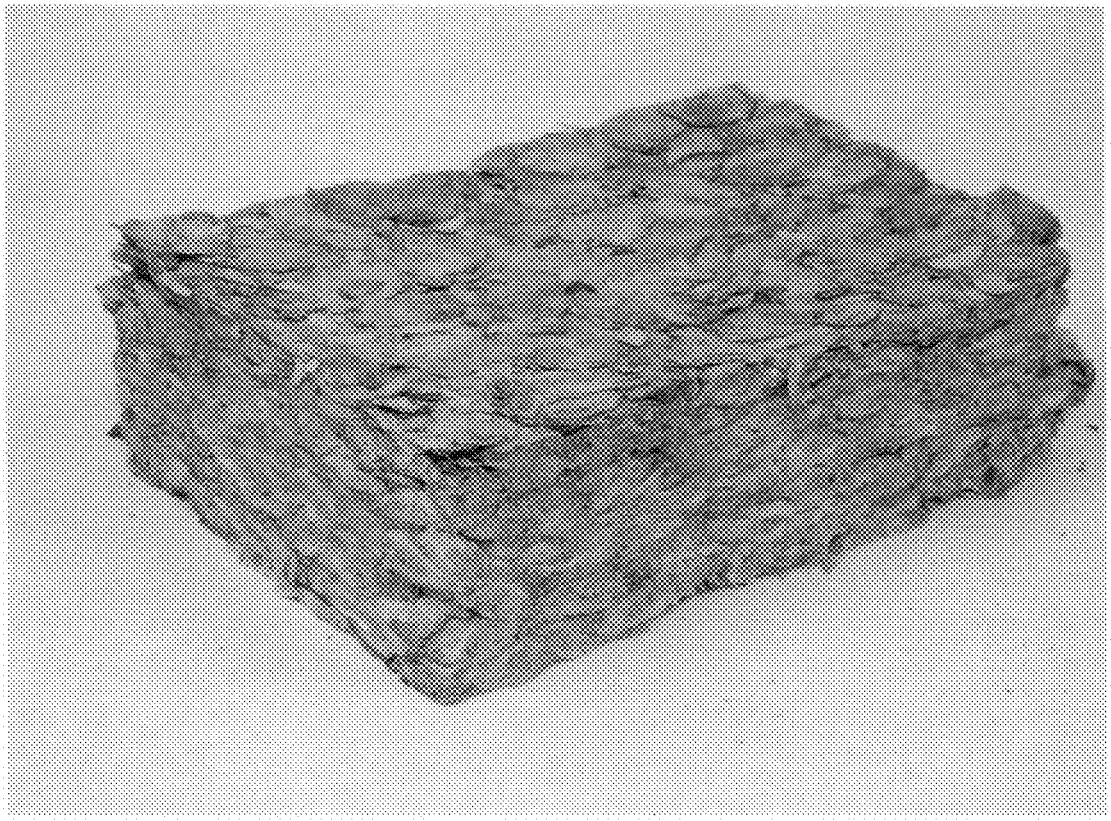

FIG. 1 illustrates cones of the 'HBC 394' hop plant;
FIG. 2 illustrates a leaf of the 'HBC 394' hop plant;
FIG. 3 illustrates the bine and leaves of the 'HBC 394' hop plant;
FIG. 4 illustrates a mature 'HBC 394' hop plant grown on a trellis;
FIG. 5 illustrates a cone of the 'HBC 394' hop plant;
FIG. 6 illustrates a leaf of the 'HBC 394' hop plant; and
FIG. 7 compressed cones of the 'HBC 394' hop plant.

The colors in these illustrations may vary with lighting conditions and, therefore, color characteristics of this new variety should be determined with reference to the observations described herein, rather than from these illustrations alone.

DETAILED BOTANICAL DESCRIPTION

The following description is based on observations made on the 16 to 17 year old plants during the 2007 and 2008 growing seasons at Toppenish, Wash. It should be understood that the characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average.

Species: *Humulus lupulus*.

Ploidy: Diploid.

Use: Brewing—aroma hop.

Disease resistance: Tolerant to powdery mildew, downy mildew, and Verticillium wilt.

Yield: 1200 to 1600 pounds/acre.

Harvest date: First week of September.

Bine:

*Color.*—Yellow green N144C, no stripe present.

*Stipule direction.*—Up.

*Stipule color.*—Yellow green N144D.

*Bine diameter.*—4.0 cm at base; 3.6 cm at 9 feet; 2.6 cm at 18 feet.

Leaf:

*Arrangement.*—Opposite.

*Shape.*—Simple.

*Average length of mature leaf.*—27 cm.

*Average width of mature leaf.*—21 cm.

*Color of mature leaf upper surface.*—Yellow green 147A.

*Color of mature leaf lower surface.*—Yellow green 147A.

*Color of immature leaf upper surface.*—Green N134A.

*Color of immature leaf lower surface.*—Green N134A.

*Number of lobes.*—5.

*Margin.*—Serrate.

*Serrations per inch.*—4.

*Average petiole length* (*mature*).—10 cm.

*Petiole color at base.*—Yellow green N144D.

*Venation.*—Palmate.

*Vein color.*—Yellow green 147A.

Cone:

*Average length.*—3.5 cm.

*Average diameter.*—1.7 cm.

*Bract tip color.*—Yellow green 149B.

*Bract base color.*—Yellow green 149B.

*Bracteole color.*—Yellow green 149C.

*Cone shape.*—Ovoid, compact.

*Bract shape.*—Ovate.

*Bract tip shape.*—Cuspidate.

*Bract tip position.*—Loosely appressed.

*Bracteole shape.*—Ovate.

*Pickability.*—Easy.

*Lupulin gland color.*—Yellow 12A.

*Aroma.*—Citrus, fruity, tropical.

Qualitative analysis:

*Alpha acids* (*as % of cone weight*).—11% to 13%.

*Beta acids* (*as % of cone weight*).—3.5% to 4.5%.

*Cohumulone* (*as % of alpha acids*).—22% to 24%.

*Myrcene* (*as % of total oils*).—60% to 65%.

*Humulene* (*as % of total oils*).—11% to 23%.

*Caryophyllene* (*as % of total oils*).—6% to 8%.

*Total oils.*—2.2 to 2.8 ml per 100 g cones.

*Storageability.*—65% to 75% alpha acids remaining after 6 months storage at room temperature.

*Essential oil profile.*—See Table 2 (on following page).

TABLE 2

Essential Oil Profile of 'HBC 394'-Gas Chromatogram

| Retention Time | Component | % |
|---|---|---|
| 10.92 | 3-methyl butyl propanoate | UDL |
| 11.56 | methyl 5-methyl-hexanoate | UDL |
| 11.79 | β-pinene | 0.93 |
| 12.30 | myrcene | 62.06 |
| 12.58 | 3-methyl-butyl 2-methyl-propanoate | 0.19 |
| 12.78 | 3-methyl-butyl 3-methyl-propanoate | 0.52 |
| 12.92 | methyl heptanoate | 0.24 |
| 13.68 | sylvestrene | 0.58 |
| 14.18 | trans-β-ocimene | 0.26 |
| 15.36 | 2-nonanone | UDL |
| 15.53 | 6,7-epoxymyrcene | UDL |
| 15.98 | linalol | 0.70 |
| 16.13 | 3-methyl-butyl 2-methyl-butanoate | UDL |
| 16.23 | 3-methyl-butyl 3-methyl-butanoate | UDL |
| 16.76 | methyl octanoate | 0.56 |
| 17.74 | (e)-3-heptenyl acetate | UDL |
| 19.45 | 2-decanone | UDL |
| 20.06 | methyl-4-nonenoate | UDL |
| 20.56 | methyl nonanoate | 0.42 |
| 21.72 | geraniol | 0.48 |
| 22.44 | (z)-3-octenyl acetate | UDL |
| 22.93 | (e)-3-octenyl acetate | UDL |
| 23.08 | 2-undecanone | 0.55 |
| 23.72 | methyl-4-decenoate | 2.27 |
| 23.79 | methyl-4,8-decadienoate | UDL |
| 24.18 | methyl geranate | 1.02 |
| 24.24 | methyl decanoate | 0.88 |
| 25.01 | octyl 2-methyl propanoate | UDL |
| 26.13 | geranyl acetate | UDL |
| 26.48 | methyl undecanoate | UDL |
| 26.68 | α-ylangene | UDL |
| 27.02 | α-copaene | UDL |
| 28.71 | caryophyllene | 8.62 |
| 28.85 | α-bergamotene | UDL |
| 29.13 | (z)-β-farnesene | UDL |
| 29.81 | humulene | 12.82 |
| 30.14 | (e)-β-farnesene | 0.16 |
| 30.30 | y-muurolene + 2-tridecanone | 1.08 |
| 30.51 | methyl-4-dodecenoate + z,e-α-farnesene | 0.18 |
| 30.63 | methyl-4,8-dodecadienoate | 1.75 |
| 30.87 | β-selinene | UDL |
| 30.99 | cis-β-guiene | 1.18 |
| 31.04 | geranyl-2-methyl propanoate | UDL |
| 31.21 | α-selinene | UDL |
| 31.49 | Δ-amorphene | 0.44 |
| 31.67 | y-cadinene | 0.72 |
| 31.81 | Δ-cadinene | UDL |
| 32.03 | zonarene | UDL |
| 32.24 | trans-cadina-1(2),4-diene | UDL |
| 32.46 | α-cadinene | UDL |
| 33.14 | selina-3,7(11)-diene | UDL |
| 33.66 | caryophyllene oxide | UDL |
| 34.40 | humulene oxide epoxide II | UDL |
| 35.04 | α-cadinol | UDL |
| 35.20 | E,Z-5,7-dodecadienyl acetate | 0.32 |
| 35.51 | Z-5-dodecenyl acetate | 0.24 |
| 35.64 | 9,12-octadecadienol | UDL |
| 35.71 | 2-heptadecanone | UDL |
| 37.06 | farnesol (isomer unknown) | 0.48 |
| 43.84 | diterpene $C_{20}H_{32}$ m.w. 272 | 0.36 |

The invention claimed is:

1. A new and distinct hop plant as shown and described herein.

* * * * *